(12) United States Patent
Monzyk

(10) Patent No.: US 7,812,279 B2
(45) Date of Patent: Oct. 12, 2010

(54) WELDING FLASH PROTECTION APPARATUS

(76) Inventor: Doug J. Monzyk, 1426 E. 8th St., Washington, MO (US) 63090

(*) Notice: Subject to any disclaimer, the term of this patent is extended or adjusted under 35 U.S.C. 154(b) by 1238 days.

(21) Appl. No.: 11/386,478

(22) Filed: Mar. 23, 2006

(65) Prior Publication Data
US 2007/0221636 A1 Sep. 27, 2007

(51) Int. Cl.
*B23K 26/00* (2006.01)
(52) U.S. Cl. .................. 219/121.63; 2/8.8; 2/9; 2/206; 128/201.27; 128/205.23; 128/202.22
(58) Field of Classification Search ......... 455/575.2, 455/445
See application file for complete search history.

(56) References Cited

U.S. PATENT DOCUMENTS

| 5,317,643 | A | * | 5/1994 | Patricelli .................. 381/376 |
| D365,666 | S | | 12/1995 | Gumpp |
| 5,749,096 | A | | 5/1998 | Fergason et al. |
| 6,070,264 | A | | 6/2000 | Hamilton et al. |
| 6,411,502 | B1 | * | 6/2002 | Burrell ..................... 361/679.3 |
| 6,841,772 | B1 | | 1/2005 | Hamilton |
| 6,855,922 | B2 | | 2/2005 | Hamilton |
| 7,089,930 | B2 | * | 8/2006 | Adams et al. .......... 128/201.27 |
| 2004/0111779 | A1 | * | 6/2004 | Gagnon et al. ..................... 2/9 |
| 2005/0002083 | A1 | | 1/2005 | Fergason |
| 2007/0056073 | A1 | * | 3/2007 | Martin et al. ................... 2/8.8 |

* cited by examiner

*Primary Examiner*—Charles N Appiah
*Assistant Examiner*—Michael T Vu
(74) *Attorney, Agent, or Firm*—Crossley Patent Law; Mark A. Crossley

(57) ABSTRACT

A welding flash protection apparatus for use with a welding machine with gas shielding is disclosed, the apparatus providing for delay of the welding flash thereby preventing the typically inherent fraction of a second delay between flash and lens darkening, hence protecting the eyes. The apparatus provides a complete helmet or apparatus components for fitment to an existing helmet. The apparatus provides a unique transmitter antenna mount for the shielding gas tank.

9 Claims, 4 Drawing Sheets

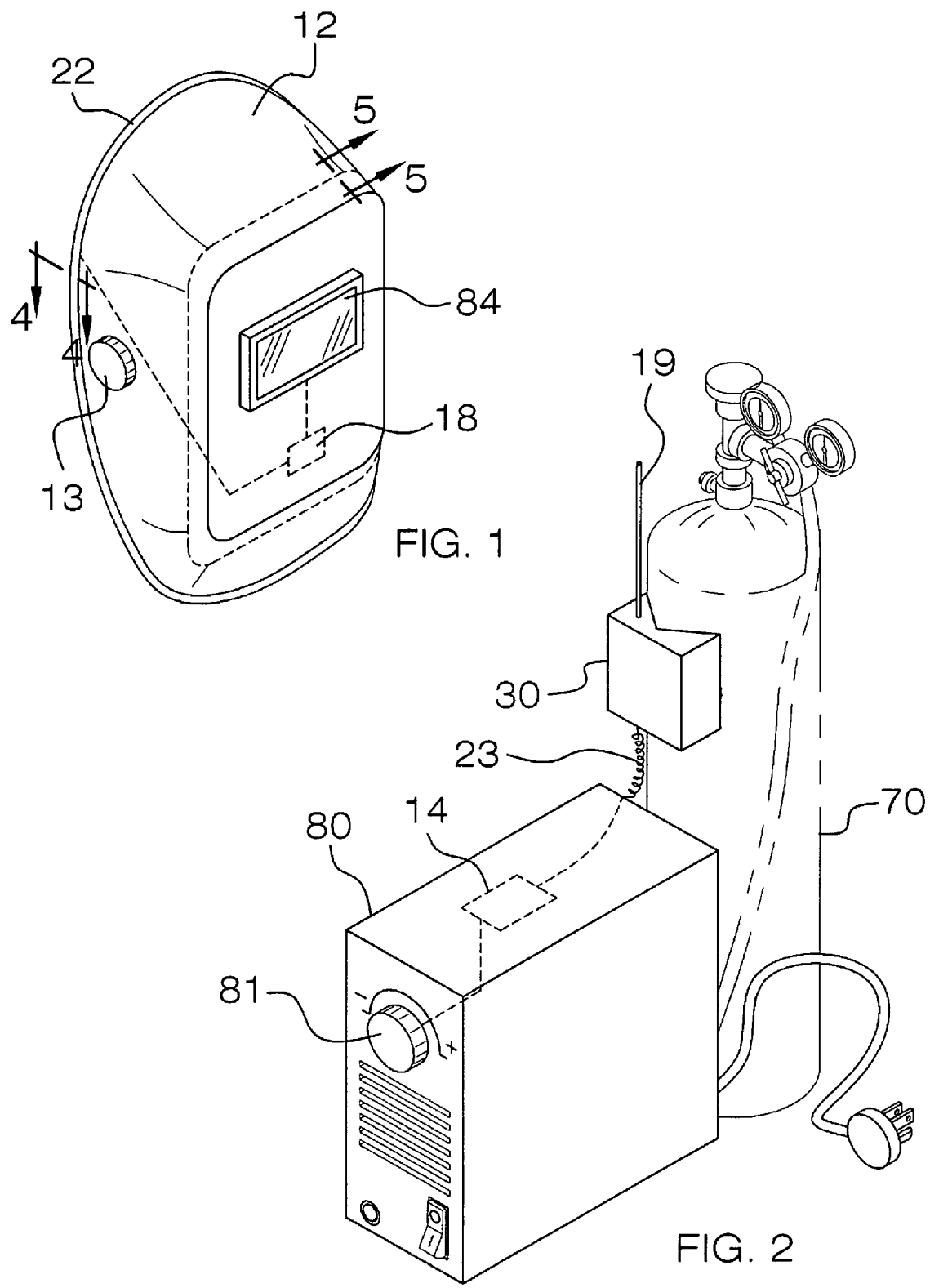

WELDING FLASH PROTECTION APPARATUS

BACKGROUND OF THE INVENTION

Welding helmets are generally comprised of a shell with a frontal lens through which a welder views work in progress. A useful improvement to such helmets has been developed. The improvement features a photochromatic lens or shutter assembly. Without the automatic darkening lens, a welder must raise and lower his helmet to view and prepare for welding. The photochromatic lens typically uses an electronic circuit which automatically darkens the lens when a welding flash is detected. A cessation of welding flash or light returns the lens to a lighter shade for viewing. While this feature is valuable in saving eyes, there is an inherent flaw. The darkening of the lens does not occur instantly. The time delay before darkening, although typically a fraction of a second, is still both dangerous to eyes and inconvenient. The present invention solves the problem of delay between the time of welding flash and lens darkening.

1. Field of the Invention

The present invention relates to welding machines and helmets with photochromatic lens and more specifically to a welding flash protection apparatus that provides for darkening of the lens without delay between welding flash and darkening.

2. Description of the Prior Art

Prior related art focuses primarily on the circuitry of photochromatic welding lenses. Such equipment compliments, but does not replace the present invention.

U.S. Pat. No. 6,070,264 issued on Jun. 6, 2000 to Hamilton et al teaches a welding helmet having a darkening and manually adjustable lens shade control. The helmet would benefit from the addition of the present invention in that the present invention prevents delay between the time of welding flash and the darkening of a lens.

U.S. Pat. No. 6,841,772 issued on Jan. 11, 2005 to Hamilton teaches an eye protection device having dual high voltage switching. The present invention would compliment this device by preventing a delay between a welding flash and darkening of a lens.

U.S. Pat. No. 6,844,922 issued on Feb. 15, 2005 to Hamilton teaches lower power phototransistor-based welding providing reduced sensitivity to low intensity light. However, it does not address the issue of a delay between welding flash and lens darkening as does the present device.

Prior art devices can fail if the photosensor lens become blocked out while view of the arc remains clear. This allows for retinal damaging light to penetrate the lens. My device overcomes this problem by allowing the lens to darken independent of the photosensitivity of a given lens.

While the above-described devices fulfill their respective and particular objects and requirements, they do not describe a welding flash protection apparatus that provides for the advantages of the present invention. Therefore, a need exists for an improved welding flash protection apparatus. In this respect, the present invention substantially departs from the conventional concepts and designs of the prior art.

SUMMARY OF THE INVENTION

The general purpose of the welding flash protection apparatus, described subsequently in greater detail, is to provide a welding flash protection apparatus which has many novel features that result in an improved welding flash protection apparatus which is not anticipated, rendered obvious, suggested, or even implied by prior art, either alone or in combination thereof.

To attain this, the present invention essentially comprises an apparatus for fitting to a welding machine and to a welding helmet. Another embodiment offers components for the welding machine and a complete welding helmet already fitted with the needed part of the invention.

The components of the present invention fitted to the welding machine delay the signal for the machine to begin welding by a fraction of a second. The delay enables the microprocessor/transmitter of the present invention to send a signal to the helmet prior to welding flash. The signal is received by the signal device of the present invention which is in communication with the photochromatic lens of the helmet. The lens is thereby able to darken upon welding flash and not after, as is typical of the current devices known in the art. Typically, the delay between the welding flash and the lens darkening startles the welder's eyes, and can damage them. The present device prohibits this eye-damaging event.

Thus has been broadly outlined the more important features of the improved welding flash protection apparatus so that the detailed description thereof that follows may be better understood and in order that the present contribution to the art may be better appreciated.

It is therefore an object of the welding flash protection apparatus to shield a welder's eyes from the bright illumination of welding device activities.

It is also an object of the welding flash protection apparatus to utilize photochromatic lenses of known welding protective devices.

It is a further object of the welding flash protection apparatus to provide welding flash protection without delay between the flash and photochromatic lens darkening.

It is an added object of the welding flash protection apparatus to provide for fitment to existing helmets and welding machines.

And, it is an object of the welding flash protection apparatus to provide a welding helmet complete with flash protection.

These together with additional objects, features and advantages of the improved welding flash protection apparatus will be readily apparent to those of ordinary skill in the art upon reading the following detailed description of presently preferred, but nonetheless illustrative, embodiments of the improved welding flash protection apparatus when taken in conjunction with the accompanying drawings. In this respect, before explaining the current embodiments of the improved welding flash protection apparatus in detail, it is to be understood that the invention is not limited in its application to the details of construction and arrangements of the components set forth in the following description or illustration. Those skilled in the art will appreciate that the concept of this disclosure may be readily utilized as a basis for the design of other structure, methods, and systems for carrying out the several purposes of the improved welding flash protection apparatus. It is therefore important that the claims be regarded as including such equivalent constructions insofar as they do not depart from the spirit and scope of the present invention. It is also to be understood that the phraseology and terminology employed herein are for purposes of description and should not be regarded as limiting.

BRIEF DESCRIPTION OF THE DRAWINGS

FIG. 1 is a perspective view.

FIG. 2 is a perspective view of a welding machine with the antenna and microprocessor installed.

DETAILED DESCRIPTION OF THE DRAWINGS

Figure 3:
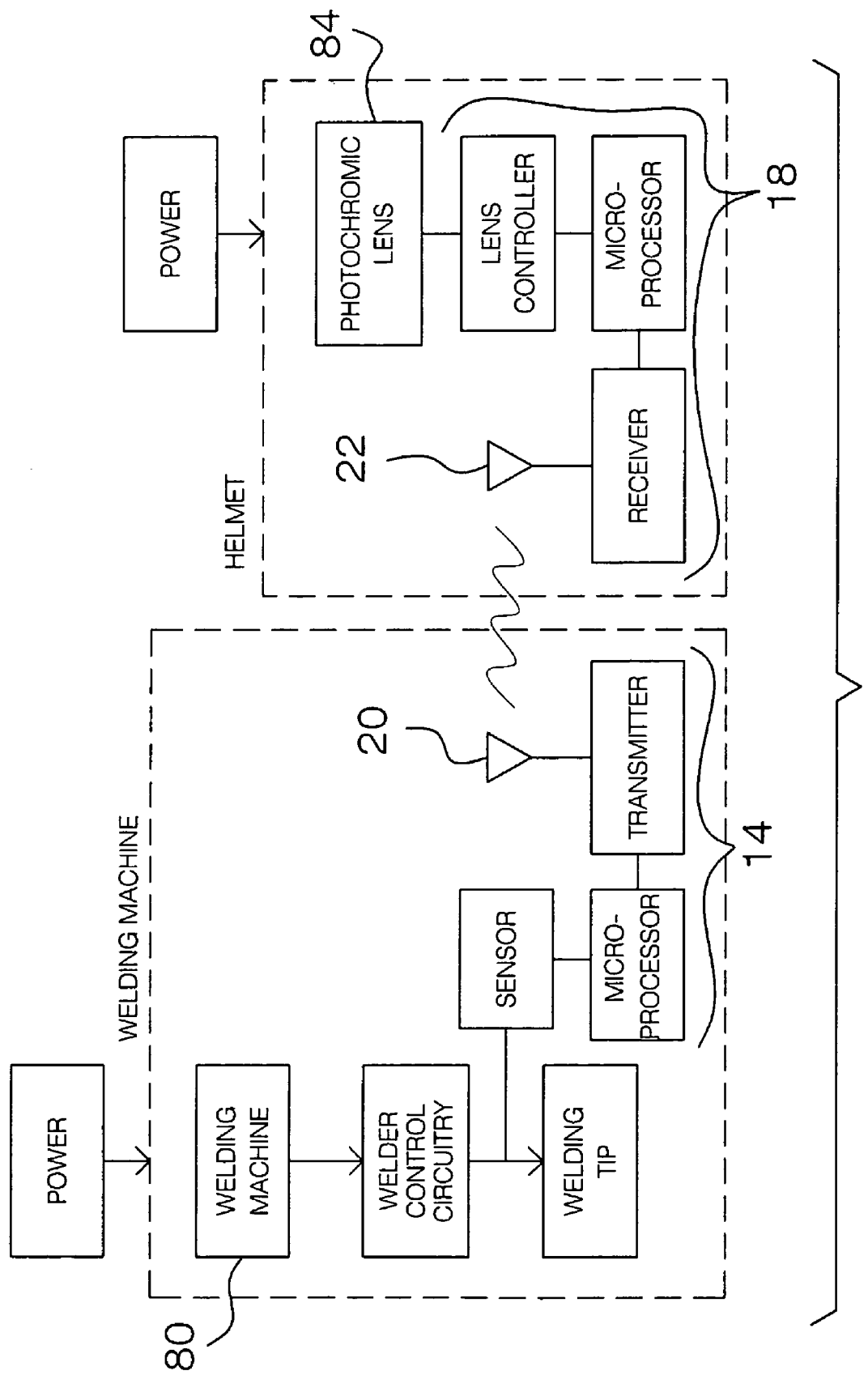
FIG. 3 is schematic block diagram of the interaction of the present device with a welding machine and helmet.

With reference now to the drawings, and in particular FIGS. 1 through 7 thereof, example of the employing the principles and concepts of the present invention and generally designated by the reference number 10 will be described.

Referring to FIGS. 1 and 2, the invention 10 comprises welding flash protection apparatus for use with a welding machine 80 with a shielding gas tank 70 and for use with a welding helmet 12 with a photochromatic lens 84. The typical welding machine has a welder control 81 for welding intensity. The invention 10 further comprises, in combination, a combined microprocessor/transmitter 14. The microprocessor/transmitter 14 fits within an existing welding machine 80. The microprocessor/transmitter 14 is connected to the internal electrics of the machine 80 such that the welding arc of the machine 80 is delayed until after a signal is sent from the microprocessor/transmitter 14 to the signal device 18 connected to the helmet 12. The signal is sent via the transmitter antenna 20 to the receiver antenna 22. The transmitter antenna 20 is in communication with the microprocessor/transmitter 14. Communication is via either wire 23 as illustrated or via airwave (not shown).

The transmitter antenna 20 is preferably connected to the shielding gas tank 70 via the tank block 30. The receiver antenna 22 is generally connected to the helmet 12 via the plurality of receiver antenna mounts 50 A or 50B. The frequency control 13 is mounted to the helmet 12 and communicates with the signal device 18 and the receiver antenna 22. The frequency control 13 enables a welder to set the frequency such that a plurality of welders and welding machines 80 using the invention 10 are not confused as to delay control. The photochromatic lens 84 of the helmet 12 is clear until receiving signal from the signal device 18, at which point the lens 84 darkens instantly. Cessation of signal allows the lens 84 to return to lightened condition.

Referring to FIG. 3, the schematic block diagram illustrates the interaction of the invention 10 with the welding machine 80 and the helmet 12. The welding machine 80 comprises a welder control circuitry. The circuitry commands the welding tip. A sensor of the invention 10 is electrically connected between the control circuitry and the tip. The sensor communicates with the microprocessor/transmitter 14. The sensor delays signal from the control circuitry to the welding tip for a fraction of a second. During this delay, the microprocessor/transmitter 14 sends an airwave signal via the transmitter antenna 20. The airwave signal is received by the receiver antenna 22. The receiver antenna 22 is in communication with the receiver and microprocessor and lens controller, all of which comprise the signal device 18. The signal device 18 communicates with the photochromatic lens 84 to activate instant darkening. The photochromatic lens 84 is well known in welding arts.

Figure 4:
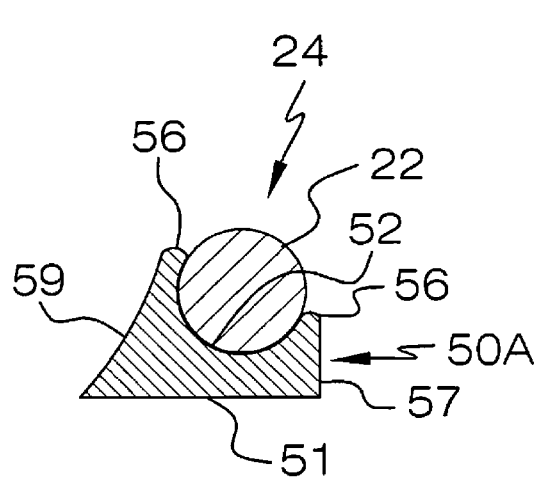
FIG. 4 is cross sectional view of the antenna and one example of an antenna clip.

Referring to FIG. 4, the example of the receiver antenna mount 50A comprises two opposing sides, the concave side 59 and the rising side 57. The mounting surface 51 connects to concave side 59 and rising side 57. An opposing clip 56 is disposed atop each of the concave side 59 and the rising side 57. A line drawn across the tops of the spaced apart clips 56 preferably comprise a 45 degree angle with respect to the plane of the mounting surface 51. The concave antenna receptacle 52 is disposed between the two opposing clips 56. The substantially circular receiver antenna 22 has a length which generally encircles at least half of the outer circumference of the welding helmet 12. The receiver antenna 22 inserts into the receptacle 52.

Figure 5:
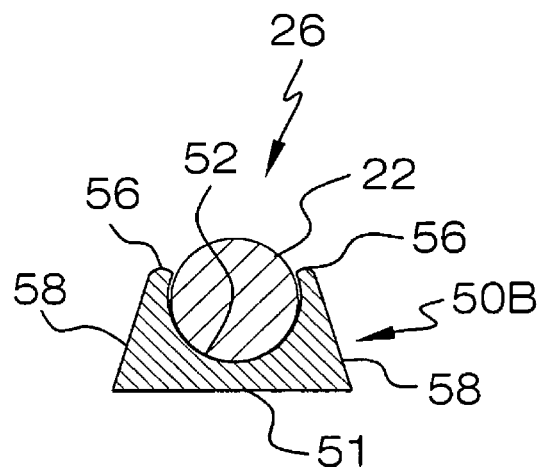
FIG. 5 is a cross sectional view of the antenna and alternate antenna clip example.

Referring to FIG. 5, another example of the receiver antenna mount 50B comprises the mounting surface 51. The mounting surface 51 is connected to each of the opposing spaced apart straight sides 58. A clip 56 is disposed atop each straight side 58. The antenna receptacle 52 is disposed between the two straight sides 58 and their respective spaced apart clips 56. The receiver antenna 22 fits within the receptacle 52.

Figure 6:
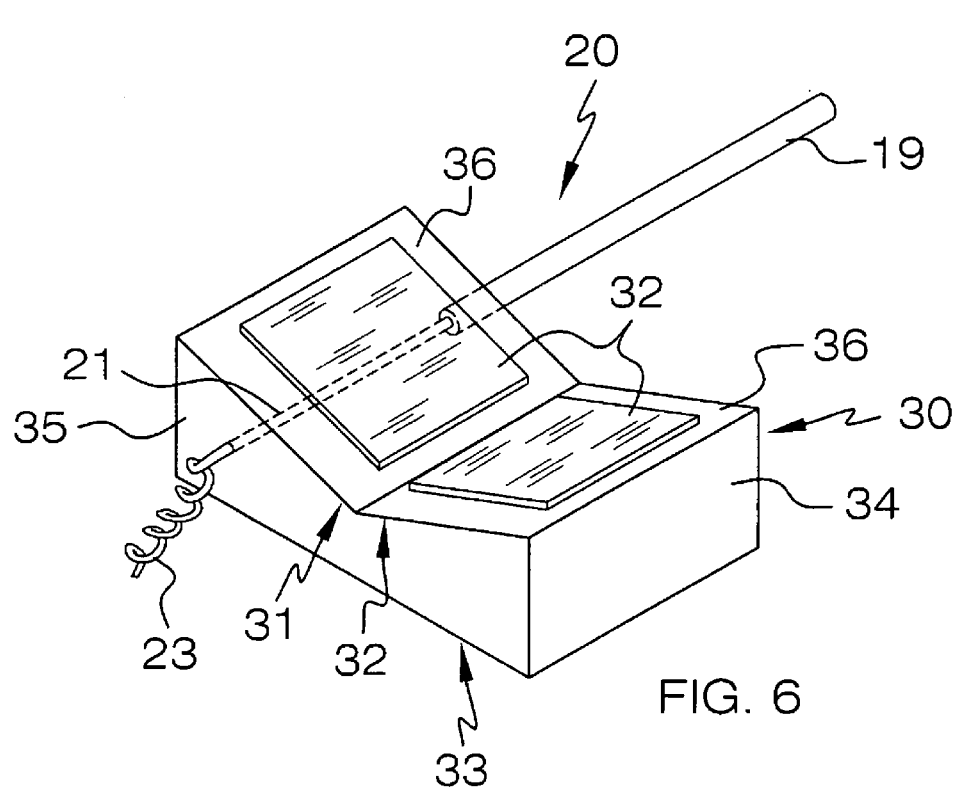
FIG. 6 is a perspective view of the tank block with antenna.

Referring to FIG. 6, the transmitter antenna 20 is comprised of a metallic stalk 21 with a transmitter antenna end 19 on the stalk 21. The stalk 21 is attracted to the tank block 30. The polyhedron tank block 30 comprises a removably affixed transmitter antenna mount for the transmitter antenna 20. The block 30 preferably removably affixes to the shielding gas tank 70. The block 30 can also removably affix to the welding machine 80. Two examples of the block 30 are offered. One example is magnetic throughout (not shown). The preferred example of the block 30 shown is FIG. 6 is fitted with a plurality of magnets 32. The block is comprised of seven sides. The sides comprise an outside 33, two opposing ends 34, two opposing sides 35, two slant sides 36, and a block V 31. The outside 33 has a length and width. The two opposing ends 34 each have a length and a width. Each end 34 is connected to the outside 33. Each of the two slant sides 36 has a length and a width. Each slant side 36 is connected to an opposing end 34. The block V 31 connects the two slant sides 36. Each of the two opposing sides 35 is connected to the outside 33. Each of the two slant sides 36 is preferably fitted with a magnet 32. The magnets 32 and the slant sides 36 and block V 31 enable the block 30 to be removably fitted to the shielding gas tank 70. The outside 33 of the block 30 is also fitted (not shown) with at least one magnet 32. The outside 33 magnet 32 enables the metallic stalk 21 to be attracted to the block 30. Additionally, the block 30 can be used to removably affix to the welding machine 80. The outside 33 magnet 32 can be fitted against the welding machine 80. Either of the slant sides 36 magnets 32 can then be used to attract the metallic stalk 21 of the transmitter antenna 20.

Figure 7:
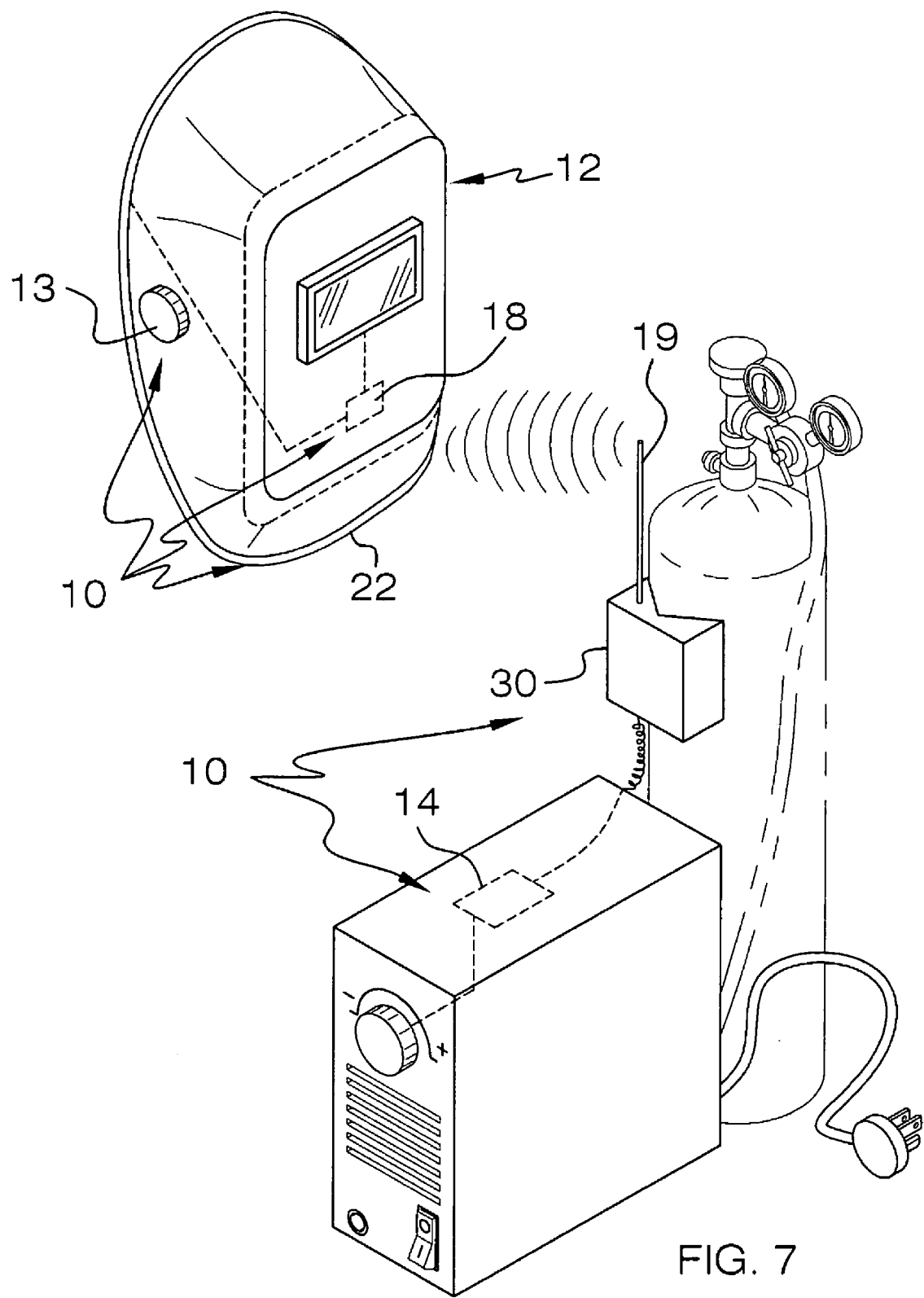
FIG. 7 is a perspective view of the helmet and the welding machine in communication.

Referring to FIG. 7, the transmitter antenna 20 signals the receiver antenna 22 of the helmet 12 via airwave.

With respect to the above description then, it is to be realized that the optimum dimensional relationships for the parts of the welding flash protection apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Directional terms such as "front", "back", "in", "out", "downward", "upper", "lower", and the like may have been used in the description. These terms are applicable to the examples shown and described in conjunction with the drawings. These terms are merely used for the purpose of description in connection with the drawings and do not necessarily apply to the position in which the present invention may be used.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A welding flash protection apparatus for use with a welding machine and a welding helmet with a photochromatic lens, the apparatus comprising, in combination:
   a combined microprocessor/transmitter;
   means for connecting the microprocessor/transmitter to the welding machine;
   a transmitter antenna in communication with the transmitter;
   a receiver antenna;
   means for connecting the receiver antenna to the welding helmet;
   a signal device, the signal device connected to the welding helmet, the signal device in communication with the receiver antenna and the photochromatic lens;
   wherein the receiver antenna is affixed to the welding helmet via a receiver antenna mount;
   wherein the receiver antenna mount is comprised of:
      a mounting surface, the mounting surface for attachment to the helmet;
      two opposing spaced apart clips of the receiver antenna mount;
      an antenna receptacle between the two opposing clips;
      a substantially circular receiver antenna, the receiver antenna having a length which encircles at least half of a circumference of the welding helmet, the receiver antenna for insertion into the receptacle of the receiver antenna mount.

2. A welding flash protection apparatus for use with a welding machine and a welding helmet with a photochromatic lens, the apparatus comprising, in combination:
   a combined microprocessor/transmitter;
   means for connecting the microprocessor/transmitter to the welding machine;
   a transmitter antenna in communication with the transmitter;
   a receiver antenna;
   means for connecting the receiver antenna to the welding helmet;
   a signal device, the signal device connected to the welding helmet, the signal device in communication with the receiver antenna and the photochromatic lens;
   wherein the transmitter antenna communicates with the microprocessor/transmitter via wire;
   wherein the receiver antenna is affixed to the welding helmet via a receiver antenna mount;
   wherein the receiver antenna mount is comprised of a plurality of receiver antenna mounts, each receiver antenna mount comprising:
      a mounting surface, the mounting surface for attachment to the helmet;
      two opposing spaced apart clips of the receiver antenna mount;
      an antenna receptacle between the two opposing clips;
      a substantially circular receiver antenna, the receiver antenna having a length which encircles at least half of a circumference of the welding helmet, the receiver antenna for insertion into the receptacle of the antenna mount.

3. A welding flash protection apparatus for use with a welding machine with a shielding gas tank, the apparatus comprising, in combination:
   a combined microprocessor/transmitter;
   means for connecting the microprocessor/transmitter to the welding machine;
   a transmitter antenna in communication with the transmitter, the antenna comprised of:
      a metallic stalk;
      a transmitter antenna end on the stalk;
   a removably affixed transmitter antenna mount tank block for the transmitter antenna, the tank block for removably affixing to the shielding gas tank or the welding machine;
   a welding helmet, the helmet having an outer circumference;
   a photochromatic lens in the welding helmet;
   a receiver antenna;
   a plurality of receiver antenna mounts, each receiver antenna mount comprising:
      two opposing sides;
      a mounting surface, the mounting surface connecting to each side;
      two opposing clips of the receiver antenna mount, each clip atop an opposing side;
      a concave antenna receptacle between the two opposing clips;
   a substantially circular receiver antenna, the receiver antenna having a length which encircles at least half of the outer circumference of the welding helmet, the receiver antenna for insertion into the receptacle of the antenna mount;
   a signal device, the signal device connected to the welding helmet, the signal device in communication with the receiver antenna and the photochromatic lens.

4. The apparatus in claim 3 wherein the transmitter tank block is magnetic.

5. The apparatus in claim 4 wherein the tank block is a polyhedron.

6. The apparatus in claim 5 wherein the polyhedron is comprised of seven sides, the sides comprising:
   an outside having a length and a width;
   two opposing ends, each end having a length and a width, each end connected to the outside;
   two slant sides, each slant side having a length and a width, each slant side connected to an opposite end;
   a block V connecting the two slant sides;
   two opposing sides, each of the opposing sides connected to the outside, the opposing ends, one slant side, and the block V.

7. The apparatus in claim 3 wherein the tank block is affixed with a plurality of magnets.

8. The apparatus in claim 7 wherein the tank block is a polyhedron.

9. The apparatus in claim 8 wherein the polyhedron is comprised of seven sides, the sides comprising:
   an outside having a length, the outside fitted with at least one of the magnets;
   two opposing ends, each end connected to the outside;
   two slant sides, each slant side connecting to an opposite end, each slant side affixed with at least one magnet;
   a block V connecting the two slant sides;
   two opposing sides, each of the opposing sides connected to the outside, the opposing ends, one slant side, and the block V.

* * * * *